US009361561B2

(12) United States Patent
Bown et al.

(10) Patent No.: US 9,361,561 B2
(45) Date of Patent: Jun. 7, 2016

(54) HIGH-RESOLUTION TRACKING OF INDUSTRIAL PROCESS MATERIALS USING TRACE INCORPORATION OF LUMINESCENT MARKERS (75) Inventors: Mark Bown, Victoria (AU); John Kraft, New South Wales (AU); Anton Launikonis, Victoria (AU); Peter Osvath, Victoria (AU); Gerhard Frederick Swiegers, Victoria (AU)

(73) Assignee: DATATRACE DNA PTY, New South Wales (AU)

( * ) Notice: Subject to any disclaimer, the term of this patent is extended or adjusted under 35 U.S.C. 154(b) by 242 days.

(21) Appl. No.: 11/919,979

(22) PCT Filed: May 10, 2006

(86) PCT No.: PCT/AU2006/000608
§ 371 (c)(1),
(2), (4) Date: Nov. 25, 2008

(87) PCT Pub. No.: WO2006/119561
PCT Pub. Date: Nov. 16, 2006

(65) Prior Publication Data
US 2009/0084981 A1   Apr. 2, 2009

(30) Foreign Application Priority Data
May 10, 2005 (AU) ................ 2005902346

(51) Int. Cl.
*G01J 1/58* (2006.01)
*G06K 19/06* (2006.01)
(Continued)

(52) U.S. Cl.
CPC ...... *G06K 19/06009* (2013.01); *G01N 21/8806* (2013.01); *G01N 2021/6439* (2013.01); *G01N 2201/0221* (2013.01); *G06K 2017/0045* (2013.01); *G06K 2017/0051* (2013.01)

(58) Field of Classification Search
CPC .... G01N 21/645; G01N 15/10; G01N 33/582

USPC ....................................................... 250/461.1
See application file for complete search history.

(56) References Cited

U.S. PATENT DOCUMENTS 4,150,295 A * 4/1979 Wieder ...................... 250/458.1
4,387,112 A * 6/1983 Blach ................................ 427/7
(Continued)

FOREIGN PATENT DOCUMENTS

EP          1 510 357        3/2005
JP         2002-505426       2/2002
(Continued)

OTHER PUBLICATIONS

Talapin et al.,Highly Luminescent Monodisperse CdSe and ScSe/ZnS Nanocrystals Synthesized in a Hexadecylamine-Trioctylphosphine Ocide-Trioctylphospine Mixture, 2001,American Chemical Soicity, Voi. 1, No. 4, 207-211.*

(Continued)

*Primary Examiner* — David Porta
*Assistant Examiner* — Djura Malevic
(74) *Attorney, Agent, or Firm* — Nixon & Vanderhye PC (57) ABSTRACT A method of marking an industrial process material including selectively incorporating a luminescent marker onto and/or into the industrial process material in a trace amount insufficient to be optically detectable in the presence of ambient light but sufficient to be non-destructively optically detectable in and/or on the industrial proce material in situ in the field or on-site. The trace amount of the luminescent marker is used to track, identify authenticate the industrial process material for at least one of material control, inventory control, stock control, logistics control, quality control and pollution control.

13 Claims, 5 Drawing Sheets (51) Int. Cl.
G01N 21/88 (2006.01)
G06K 17/00 (2006.01)
G01N 21/64 (2006.01)

(56) References Cited

U.S. PATENT DOCUMENTS

| | | | |
|---|---|---|---|
| 4,485,308 A * | 11/1984 | Rabatin | 250/461.1 |
| 4,546,416 A * | 10/1985 | Pemberton | 362/84 |
| 4,549,081 A | 10/1985 | Ace | |
| 4,565,022 A * | 1/1986 | Chapin | 40/442 |
| 4,598,205 A | 7/1986 | Kaule et al. | |
| 4,675,529 A | 6/1987 | Kushida | |
| 4,703,572 A * | 11/1987 | Chapin | 40/442 |
| 5,296,380 A * | 3/1994 | Margalit | 436/106 |
| 5,422,719 A | 6/1995 | Goldstein | |
| 5,498,280 A * | 3/1996 | Fistner | C09D 13/00 106/31.64 |
| 5,569,317 A * | 10/1996 | Sarada et al. | 524/111 |
| 5,714,758 A | 2/1998 | Neu | |
| 5,736,410 A * | 4/1998 | Zarling | B82Y 15/00 250/458.1 |
| 5,986,550 A * | 11/1999 | Rapaport et al. | 340/572.3 |
| 6,123,871 A * | 9/2000 | Carroll | C09K 11/06 252/301.36 |
| 6,142,380 A * | 11/2000 | Sansone et al. | 235/487 |
| 6,165,609 A * | 12/2000 | Curatolo | 428/343 |
| 6,188,996 B1 * | 2/2001 | Sansone | 705/408 |
| 6,211,526 B1 * | 4/2001 | Huston et al. | 250/484.4 |
| 6,232,124 B1 * | 5/2001 | Selinfreund | 436/20 |
| 6,270,213 B1 * | 8/2001 | Sansone et al. | 347/100 |
| 6,274,873 B1 * | 8/2001 | Outwater et al. | 250/458.1 |
| 6,354,501 B1 * | 3/2002 | Outwater et al. | 235/462.01 |
| 6,380,547 B1 * | 4/2002 | Gonzalez et al. | 250/458.1 |
| 6,441,380 B1 * | 8/2002 | Lawandy | 250/458.1 |
| 6,444,143 B2 * | 9/2002 | Bawendi et al. | 252/301.6 S |
| 6,458,595 B1 * | 10/2002 | Selinfreund | 436/20 |
| 6,506,476 B1 * | 1/2003 | Kaule et al. | 428/195.1 |
| 6,512,580 B1 * | 1/2003 | Behringer et al. | 356/244 |
| 6,536,672 B1 * | 3/2003 | Outwater | 235/491 |
| 6,774,361 B2 * | 8/2004 | Bawendi et al. | 850/18 |
| 7,038,766 B2 * | 5/2006 | Kerns et al. | 356/71 |
| 7,079,230 B1 * | 7/2006 | McInerney et al. | 356/71 |
| 7,124,944 B2 * | 10/2006 | Selinfreund et al. | 235/454 |
| 7,138,009 B2 * | 11/2006 | Auslander | 106/31.32 |
| 7,175,086 B2 * | 2/2007 | Gascoyne | G01N 21/643 235/454 |
| 7,323,696 B2 * | 1/2008 | Vann et al. | 250/458.1 |
| 7,355,944 B2 * | 4/2008 | van de Grampel | G07D 7/12 369/53.1 |
| 7,369,681 B2 * | 5/2008 | Foth et al. | 382/103 |
| RE40,443 E * | 7/2008 | Sansone | 705/408 |
| 7,441,704 B2 * | 10/2008 | Ross | 235/454 |
| 7,496,938 B2 * | 2/2009 | Potyrailo | G07D 7/122 430/270.11 |
| 7,597,961 B2 * | 10/2009 | Maruvada | G11B 23/281 428/412 |
| 7,674,532 B2 * | 3/2010 | Einhorn et al. | 428/690 |
| 7,788,377 B2 * | 8/2010 | Itoh et al. | 709/226 |
| 7,812,324 B2 * | 10/2010 | Connally | G01N 21/6408 250/461.1 |
| 7,888,646 B2 * | 2/2011 | Breit et al. | 250/341.1 |
| 7,910,022 B2 * | 3/2011 | Agrawal et al. | 252/301.33 |
| 7,910,376 B2 * | 3/2011 | Menzel | 436/172 |
| 7,919,325 B2 * | 4/2011 | Eastwood et al. | 436/56 |
| 8,571,254 B2 * | 10/2013 | Ogura | 382/100 |
| 2002/0008148 A1 * | 1/2002 | Empedocles et al. | 235/494 |
| 2002/0015150 A1 * | 2/2002 | Armstrong et al. | 356/301 |
| 2002/0122878 A1 * | 9/2002 | Kerns et al. | 427/8 |
| 2002/0158211 A1 * | 10/2002 | Gillispie | G01N 21/6408 250/458.1 |
| 2002/0158212 A1 * | 10/2002 | French | B01L 3/50853 250/459.1 |
| 2003/0005304 A1 * | 1/2003 | Lawandy et al. | 713/176 |
| 2003/0006170 A1 * | 1/2003 | Lawandy | 209/3.3 |
| 2003/0036201 A1 * | 2/2003 | Nelson et al. | 436/56 |
| 2003/0133105 A1 * | 7/2003 | Gorelik et al. | 356/301 |
| 2003/0194578 A1 * | 10/2003 | Tam et al. | 428/690 |
| 2005/0083720 A1 * | 4/2005 | Fukui et al. | 365/106 |
| 2005/0092408 A1 * | 5/2005 | Lauf et al. | 149/123 |
| 2005/0178841 A1 * | 8/2005 | Jones et al. | 235/468 |
| 2005/0221351 A1 * | 10/2005 | Ryu | G01N 21/6452 435/6.11 |
| 2005/0229698 A1 * | 10/2005 | Beecroft et al. | 73/300 |
| 2005/0264001 A1 * | 12/2005 | Kerns et al. | 283/81 |
| 2005/0279248 A1 * | 12/2005 | Auslander | 106/31.28 |
| 2006/0014045 A1 * | 1/2006 | Einhorn et al. | 428/690 |
| 2006/0052251 A1 * | 3/2006 | Anderson | E21B 47/1015 507/103 |
| 2006/0131517 A1 * | 6/2006 | Ross et al. | 250/556 |
| 2006/0131518 A1 * | 6/2006 | Ross et al. | 250/556 |
| 2006/0186348 A1 * | 8/2006 | Nguyen et al. | 250/484.4 |
| 2006/0219961 A1 * | 10/2006 | Ross et al. | 250/556 |
| 2006/0234215 A1 * | 10/2006 | Hudson | 435/5 |
| 2007/0023715 A1 * | 2/2007 | Ross et al. | 250/556 |
| 2008/0025594 A1 * | 1/2008 | Metzger | 382/141 |
| 2008/0116272 A1 * | 5/2008 | Giering et al. | 235/439 |
| 2008/0121815 A1 * | 5/2008 | Agrawal et al. | 250/473.1 |
| 2008/0121818 A1 * | 5/2008 | Agrawal et al. | 250/486.1 |
| 2008/0185557 A1 * | 8/2008 | Agrawal et al. | 252/301.35 |
| 2009/0321623 A1 * | 12/2009 | Ross et al. | 250/271 |
| 2010/0320371 A1 * | 12/2010 | Agrawal et al. | 250/271 |
| 2011/0210272 A1 * | 9/2011 | Chan | C12Q 1/6809 250/459.1 |

FOREIGN PATENT DOCUMENTS

| | | |
|---|---|---|
| JP | 2003-248790 | 9/2003 |
| JP | 2003-531734 | 10/2003 |
| JP | 2004-534953 | 11/2004 |
| WO | 9801817 | 1/1998 |
| WO | WO 99/44044 | 9/1999 |
| WO | 00/17103 | 3/2000 |
| WO | 01/78288 | 10/2001 |
| WO | WO 01/78288 | 10/2001 |
| WO | 03006965 | 1/2003 |
| WO | WO 03/006965 | 1/2003 |
| WO | 2005/095926 | 10/2005 |

OTHER PUBLICATIONS

Dabbousi et al., Electroluminescence from CdSe quantum-dot/polymer composites, Mar. 13, 1995, Appl. Phys. Lett. 66 (11), 1316-1318.*

International Search Report for PCT/AU2006/000608 mailed Jul. 26, 2006.

Office Action issued on Jul. 12, 2011 in corresponding Japanese Application No. 2008-510360.

* cited by examiner

FIGURE 1

| Luminescent Materials | Prominent and Distinctive Emission Wavelengths, fmn, (in nanometres) of the luminescent materials 1-13 when irradiated with light of wavelength F1-F5: | | | | |
| --- | --- | --- | --- | --- | --- |
| | F1 | F2 | F3 | F4 | F5 |
| 1 | 370 (f11) | - | - | - | - |
| 2 | 420 (f12) | - | - | - | - |
| 3 | 490 (f13) | - | - | - | - |
| 4 | 550 (f14) | - | - | - | - |
| 5 | - | 400 (f25) | - | 470 (f45) | - |
| 6 | - | 530 (f26) | - | - | - |
| 7 | - | 672 (f27) | - | - | - |
| 8 | - | - | 590 (f38) | - | - |
| 9 | - | - | 635 (f39) | - | - |
| 10 | - | - | 650 (f310) | - | 790 (f510) |
| 11 | - | - | - | 690 (f411) | - |
| 12 | - | - | - | 720 (f412) | - |
| 13 | - | - | - | - | 650 (f513) |

FIGURE 2

*Binary Codes Describing Permutations of 13 Different Luminescent Materials*

| Luminescent materials present | 1 | 2 | 3 | 4 | 5 | 6 | 7 | 8 | 9 | 10 | 11 | 12 | 13 |
|---|---|---|---|---|---|---|---|---|---|---|---|---|---|
| all of 1-13 present | 1 | 1 | 1 | 1 | 1 | 1 | 1 | 1 | 1 | 1 | 1 | 1 | 1 |
| number 2 absent only | 1 | 0 | 1 | 1 | 1 | 1 | 1 | 1 | 1 | 1 | 1 | 1 | 1 |
| number 3 absent only | 1 | 1 | 0 | 1 | 1 | 1 | 1 | 1 | 1 | 1 | 1 | 1 | 1 |
| number 4 absent only | 1 | 1 | 1 | 0 | 1 | 1 | 1 | 1 | 1 | 1 | 1 | 1 | 1 |
| . | | | | | | | | | | | | | |
| . | | | | | | | | | | | | | |
| . | | | | | | | | | | | | | |
| . | | | | | | | | | | | | | |
| all absent except 1 and 12 | 1 | 0 | 0 | 0 | 0 | 0 | 0 | 0 | 0 | 0 | 0 | 1 | 0 |
| all absent except 1 and 13 | 1 | 0 | 0 | 0 | 0 | 0 | 0 | 0 | 0 | 0 | 0 | 0 | 1 |
| all absent except 1 | 1 | 0 | 0 | 0 | 0 | 0 | 0 | 0 | 0 | 0 | 0 | 0 | 0 |

HIGH-RESOLUTION TRACKING OF INDUSTRIAL PROCESS MATERIALS USING TRACE INCORPORATION OF LUMINESCENT MARKERS

This application is the U.S. national phase of International Application No. PCT/AU2006/000608 filed 10 May 2006 which designated the U.S. and claims priority to Australian Patent Application No. 2005902346 filed 10 May 2005, the entire contents of each of which are hereby incorporated by reference.

FIELD OF THE INVENTION

The present invention relates to high-resolution tracking of industrial process materials using trace incorporation of luminescent markers and a portable reader for detecting them.

BACKGROUND OF THE INVENTION

High-resolution tracking of materials used in industrial production processes is required for comprehensive material control, inventory control (or stock control), process control, logistics control, quality control and pollution control. These controls ensure that materials used in industrial production processes are available in the required place, at the required time, in the required quantities, and in the required quality, as well as ensuring that materials are properly accounted for from acquisition and processing, to use and disposal.

Public and private sector demand for high-resolution tracking of industrial process materials has been heightened by concerns about terrorist misuse of explosives and agrochemicals, quality and contamination of food/medicine/fuel/feed, illicit substitution of inferior materials, liability for defective products and built structures, price and availability of commodities, and pollution of the environment.

Interest in high-resolution tracking has also been driven by life-cycle thinking about materials and products. The life-cycle concept is a "cradle-to-grave" approach which recognises that materials and products have economic and environmental impacts as they pass through the life-cycle stages of raw material acquisition, processing, manufacturing, formulation, transportation, distribution, use, reuse, maintenance, recycling, disposal and waste management. Intense material tracking is required for a comprehensive life-cycle inventory, even for a simple product made of a single raw material in one or two manufacturing steps.

It is difficult to track industrial process materials that are standardised, undifferentiated, substitutable, interchangeable, batch-processed in essentially identical form, and available in bulk or from a variety of sources. Examples of such materials include primary commodities, such as agricultural and mineral products, and processed commodities, such as manufacturing materials, building materials and industrial chemicals. In practice, the low inherent visible identity of these materials defeats high-resolution tracking.

Luminescent marking has been proposed for identifying or authenticating high-value articles or materials and in particular security documents such as passports, banknotes, credit cards, cheques, as well as articles such as jewelry, vehicles, electronic goods, etc. However, prior luminescent marking systems require either relatively high amounts of luminescent materials to make detection reliable in ambient light or, when using trace amounts of luminescent materials, sophisticated and bulky laboratory spectrometers for detecting luminescence. High concentrations of luminescent materials are not practicable or cost-effective for tracking industrial process materials which are generally low-value commodity materials, typically mass-produced and sold in bulk. Furthermore, the use of laboratory detection equipment often requires detailed sample preparation by a trained analytical chemist and is not amenable to high-throughput mass screening of samples for off-site applications.

SUMMARY OF THE INVENTION

According to the present invention there is provided a method of marking an industrial process material including selectively incorporating a luminescent marker onto and/or into the industrial process material in a trace amount insufficient to be optically detectable in the presence of ambient light but sufficient to be non-destructively optically detectable in and/or on the industrial process material in situ in the field or on-site, wherein the trace amount of the luminescent marker is used to track, identify or authenticate the industrial process material for at least one of material control, inventory control, stock control, process control, logistics control, quality control and pollution control.

The present invention also provides a method for tracking an industrial process material through a plurality of life-cycle stages thereof, the method including the steps of:
  conferring a unique luminescent response on the industrial process material by selectively incorporating a trace amount of a luminescent marker therein and/or thereon; and
  identifying or authenticating the industrial process material during the plurality of life-cycle stages thereof by detecting a luminescent response from the industrial process material in situ in the field or on-site which corresponds to the unique luminescent response.

The present invention further provides a system including:
  a portable luminescence reader configured to detect, in situ in the field or on-site, unique luminescent responses conferred on industrial process materials and/or products, parts or structures formed therefrom;
  a database associatively storing information relating to the industrial process materials, products, parts and/or structures and their corresponding conferred unique luminescent responses;
  processor instructions for causing a processor to compare luminescent responses detected by the portable luminescence reader with the conferred unique luminescent responses stored in the database to identify or authenticate the industrial process materials, products, parts and/or structures.

The present invention also provides a portable luminescence reader including a spectrometer light source and a spectrometer detector the optical paths of which are commonly arranged inside an opaque shroud with an opening defining a sample area, wherein the spectrometer light source and the spectrometer detector are substantially parfocal on the sample area, and wherein the opaque shroud substantially occludes ambient light from the spectrometer detector when the opening is substantially occluded by a sample.

BRIEF DESCRIPTION OF THE DRAWINGS

The present invention will now be described by way of non-limiting examples only with reference to the accompanying drawings in which:

FIG. 5A is a perspective exploded view of an integrated portable luminescence reader according to an embodiment of the present invention, while

DESCRIPTION OF THE EMBODIMENTS

As used herein the term "luminescent marker" refers to a material or mixture of materials which display fluorescence or phosphorescence (emission of light) as a result of a previous non-thermal energy transfer. Where, for example, a luminescent material is incorporated on and/or into an industrial process material according to any of the methods of the present invention, the industrial process material is said to be "marked" by the luminescent material. In this way the luminescent material is acting as a "luminescent marker" for that particular industrial process material. This marker may be selected from one or more luminescent materials which each provide a unique luminescent response when incorporated in and/or on the industrial process material. In this way the addition of the trace amount of the luminescent marker confers a unique identity to that industrial process material. The one or more luminescent materials respectively comprising the luminescent markers may be chosen to provide the unique identity by taking advantage of their unique luminescent profiles, for example, their excitation and emission frequencies and intensities A luminescent marker can therefore include one or more luminescent materials which individually or collectively have a unique luminescent emission and/or excitation profile.

Examples of luminescent materials which may be used individually or in combination as a luminescent marker in the methods of the present invention include:

a) Luminescent Organic Materials Including the Following:

Aromatic and heteroaromatic monomers, such as pyrene, anthracene, naphthalene, fluorescein, coumarin, biphenyl, fluoranthene, perylene, phenazine, phenanthrene, phenanthridine, acridine, quinoline, pyridine, primulene, propidinium halide, tetrazole, maleimide, carbazole, rhodamine, naphthol, benzene, ethidium halide, ethyl viologen, fluorescamine, pentacene, stilbene, p-terphenyl, porphyrins, triphenylene, umbelliferone, and their derivatives, such as, 9-anthracenylmethyl acrylate, 2-naphthylacrylate, 9-vinylanthracene, 7-[4-(trifluoromethyl)coumarin]acrylimide, 2-aminobiphenyl, 2-aminopyridine, bis-N-methylacridinium nitrate, diacetylbenzene, diaminobenzene, dimidium bromide, methylpyrene, 2-naphthol, 3-octadecanoylumbelliferone.

Fluorescent dyes known by trade names, such as Acid Yellow 14, Acridine Orange, Acridine Yellow G, Auramine O, Azure A and B, Calcein Blue, Coumarins 6, -30, -6H, -102, -110, -153, -480d, Eosin Y, Evans Blue, Hoechst 33258, Methylene Blue, Mithramycine A, Nile Red, Oxonol VI, Phloxine B, Rubrene, Rose Bengal, Unalizarin, Thioflavin T, Xylenol Orange, and their derivatives, such as Cresyl Violet perchlorate, 1,9-dimethylene blue, dodecylacridine orange bromide.

Polymers, such as fluorescent polymers, like poly(pyromellitic dianhydride-alt-3,6-diaminoacridine), poly((4,4'-hexafluoroisopropylidene)diphthalic anhydride-alt-thionin), light-emitting conjugated polymers, like polyfluorenyls, polyacetylenes, polyphenylene ethynelenes, and polyphenylene vinylenes.

Light-emitting dopant functionalised polymers, such as poly(9-anthracenylmethyl methacrylate), poly[(methylmethacrylates-co-(fluorescein O-acrylate)], poly[(methylmethacrylates)-co-(9-anthracenylmethyl acrylate)].

b) Luminescent Metal Complexes Including the Following:

Metal complex emitters, such as zinc-, gold-, palladium-, rhodium-, iridium-, silver-, platinum-, ruthenium-, boron-, europium-, indium-, samarium-, and rare earth-complexes in general of a wide range of ligands, and their derivatives, such as bis(8-hydroxyquinolato)zinc, (2,2'-bipyridine)dichloropalladium(II), (2,2'-bipyridine)dichloroplatinum(II), chlorobis(2-phenylpyridine) rhodium(III), 8-hydroxyquinoline aluminium salt, lithium tetra(8-hydroxyquinolinato)boron, tris(dibenzoylmethane) mono(5-aminophenanthroline)europium (III), trichlorotris(pyridine)iridium(III). Other examples are provided in the following scientific papers: "*Metallated molecular materials of fluorene derivatives and their analogues*": Coordination Chemistry Reviews Volume: 249, Issue: 9-10, May, 2005, pp. 971-997; and "*Luminescent molecular sensors based on analyte coordination to transition-metal complexes*", Coordination Chemistry Reviews Volume: 233-234, Nov. 1, 2002, pp. 341-350.

c) Phosphors (Where the Species Below Denote Both Doped, as Well as Undoped Systems; that is, for Example, CaS:Tb,Cl Refers to CaS (Undoped), CaS:Tb-Doped, and CaS:Cl-Doped) and Includes the Following:

Oxides, such as CaO:Eu, CaO:Eu,Na, CaO:Sm, CaO:Tb, $ThO_2$:Eu, $ThO_2$:Pr, $ThO_2$:Tb, $Y_2O_3$:Er, $Y_2O_3$:Eu, $Y_2O_3$:Ho, $Y_2O_3$:Tb, $La_2O_3$:Eu, $CaTiO_3$:Eu, $CaTiO_3$:Pr, $SrIn_2O_4$:Pr,Al, $SrY_2O_4$:Eu, $SrTiO_3$:Pr,Al, $SrTiO_3$:Pr, $Y(P,V)O_4$:Eu, $Y_2O_3$:Eu, $Y_2O_3$:Tb, $Y_2O_3$:Ce,Tb, $Y_2O_2S$:Eu, $(Y,Gd)O_3$:Eu, $YVO_4$:Dy.

Silicates, such as $Ca_5B_2SiO_{10}$:Eu, $Ba_2SoO_4$:Ce,Li,Mn, $CaMgSi_2O_6$:Eu, $CaMgSi_2O_6$:Eu/Mn, $Ca_2MgSi_2O_7$:Eu/Mn, $BaSrMgSi_2O_7$:Eu, $Ba_2Li_2Si_2O_7$:Sn, $Ba_2Li_2Si_2O_7$:Sn,Mn, $MgSrBaSi_2O_7$:Eu, $Sr_3MgSi_2O_8$:Eu,Mn, $LiCeBa_4Si_4O_{14}$:Mn, $LiCeSrBa_3Si_4O_{14}$:Mn.

Halosilicates, such as $LaSiO_3Cl$:Ce,Tb.

Phosphates, such as $YPO_4$:Ce,Tb, $YPO_4$:Eu, $LaPO_4$:Eu, $Na_3Ce(PO_4)_2$:Tb.

Borates, such as $YBO_3$:Eu, $LaBO_3$:Eu, $SrO.3B_2O_3$:Sm, $MgYBO_4$:Eu, $CaYBO_4$:Eu, $CaLaBO_4$:Eu, $LaALB_2O_6$:Eu, $YAl_5B_4O_{12}$:Eu, $YAlsB_4O_{12}$:Ce,Tb, $LaAl_3B4O_{12}$:Eu, $SrB_8O_{13}$:Sm, $CaYB_{0.8}O_{3.7}$:Eu, $(Y,Gd)BO_3$:Tb, $(Y,Gd)BO_3$:Eu.

Aluminates and Gallates, such as $YAlO_3$:Eu, $YAlO_3$:Sm, $YAlO_3$Tb, $LaAlO_3$:Eu, $LaAlO_3$:Sm, $Y_4Al_2O_9$:Eu, $Y_3Al_5O_{12}$:Eu, $CaAl_2O_4$:Tb, $CaTi_{0.9}Al_{0.1}O_3$:Bi, $CaYAlO_4$:Eu, $MgCeAlO_{19}$:Tb, $Y_3Al_5O_{12}$:Mn.

Miscellaneous oxides, such as $LiInO_2$:Eu, $LiInO_2$:Sm, $LiLaO_2$:Eu, $NaYO_2$:Eu, $CaTiO_3$:Pr, $Mg_2TiO_4$:Mn, $YVO_4$:Eu, $LaVO_4$:Eu, $YAsO_4$:Eu, $LaAsO_4$:Eu, $Mg_8Ge_2O_{11}F_2$:Mn, $CaY_2ZrO_6$:Eu.

Halides and oxyhalides, such as $CaF_2$:Ce/Tb, $K_2SiF_6$:Mn, YOBr:Eu, YOCl:Eu, YOF:Eu, YOF:Eu, LaOF:Eu, LaOCl:Eu, $(ErCl_3)_{0.25}(BaCl_2)_{0.75}$, LaOBr:Tb, LaOBr:Tm.

CaS-type sulfides, such as CaS:Pr,Pb,Cl, CaS:Tb, CaS:Tb,Cl.

Miscellaneous sulfides and oxysulfides, such as $Y_2O_2S:Eu$, $GdO_2S:Tb$, $Na_{1.23}K_{0.42}Eu_{0.12}TiSi_5O_{13}:xH_2O:Eu$.

Lamp and cathode ray tube phosphors, including rare-earth doped phosphors.

"Up-converters" or compounds that emit photons of higher energy than they absorb, such as $NaYF_4:Er,Yb$, $YF_3:Er,Yb$, $YF_3:Tm,Yb$.

d) Quantum-Dots or Nanoparticulate Materials whose Luminescent Properties are Dependent on their Particulate Size, Such as Gold and Other Metal Nanoparticles.

Due to the cost associated with many of the luminescent materials described above, their natural presence in industrial process materials is rare which makes them suitable candidates as markers.

Furthermore, the luminescent marker is suitably selected from one or more luminescent materials which do not adversely affect the physical properties or react with the industrial process material either during process manufacture or during storage, transport or in use. To ensure that the marker remains inert with respect to the industrial process material the luminescent materials which comprise the marker may be chemically or physically modified. For instance, the luminescent marker may be composed of one or more luminescent materials which are physically encapsulated within a covering sheath. The sheath may be composed of a polymer, such as methylmethacrylate, polypropylene, polyethylene, or polystyrene or a wax such as paraffin wax, beeswax, gel wax, vegetable wax or the like. Methods of encapsulating luminescent materials with polymers and waxes are known in the art.

For industrial process materials having long life-cycles, the one or more luminescent materials used in the luminescent marker should be selected to be those which do not degrade easily over time and therefore can be tracked for long periods. Examples of longer-lived luminescent materials potentially suitable for use as a luminescent marker may include Ag-activated zinc sulfide, Mn-activated magnesium fluorogeminate (in surface settings, exposed to sunlight), pyrene and anthracene (within the body in bulk settings, not exposed to sunlight). The luminescence properties of these luminescent materials degrade slowly over time so that they can be reliably and reproducibly detected over extended periods of time which substantially or at least partially correspond to the duration of the average life-cycle of the associated industrial process material.

As used herein the term "industrial process material" includes, but is not limited to the following classes of materials:

a) Materials Used for Construction, Including:
Concrete
Cement
Timber
Treated timber
Clays and Clay Products
Glass
Structural plastics and polymers
Decorative plastics and polymers
Sealing plastics and polymers
Composite materials
Ceramics
Metals and metal alloys
Gypsum
Bitumen
Asphalt and asphaltic concrete
Paint
Corrosion protection materials, such as paint
Silicon
Structural textiles b) Materials Used for Structural and Non Structural Applications in Transportation Vehicles, Including Motor Vehicles, Motorcycles, Boats, Air-Transportation Vehicles, and the like, Such Materials Including:
Rubber, vulcanised rubber and their compounds
Silicon
Plastics
Composite materials
Epoxy
Ceramic materials and ceramic composites
Compounded materials such as, but not limited to, brake pads
Adhesive, glue, (vehicle) cement
Metal and metal alloys
Glass
Polycarbonate
Paints, undercoats and primers
Finishing products such as abrasive compounds, polishes and sealants
Antifouling materials and compounds
Low friction materials and compounds
Antistatic compounds
Lubricants
Cooling materials and compounds
Hydraulic fluids
Anti corrosion additives and compounds
Textiles c) Materials Used for Industrial Manufacturing of Goods, Components, Clothing, and Chattels, Including:
Plastics and polymers and composites used as substrates for removable media such as, but not limited to memory cards and electronic chips
Plastics and polymers and composites used as base materials for computers, phones, batteries, and plastic utensils and components, toys
Glass
Composite materials for structural purposes
Epoxy
Glue
Ceramics
Semiconductors
Textiles d) Materials Used in the Industrial Manufacturing of Computers and Information Technology-Based Items, Including:
Ceramics
Plastics
Polymers
Composite materials
Components such as circuit boards, processors and memory chips e) Materials Used for Large-Scale Industrial Packaging of Goods, Components, and Chattels, Including:
Paper
Cardboard
Plastics
Textiles f) Materials Used in Primary and Energy Industries, Including:
Bulk materials used as commercial commodity chemicals and commodity materials
Propellants
Energetic materials
Politically sensitive materials and chemicals
Cyanide Precursor chemicals
Nuclear materials
Aggregates
Ores and processed and semi-processed ores
Ammonium nitrate
Other nitrates
Pesticide, herbicides and other potentially dangerous materials
Soil conditioners
Scrubbing agents
Mineral and agricultural commodities that are exchanged on commodity trading floors g) Materials Used in Miscellaneous Industrial Manufacturing, Including:
Pharmaceuticals and their precursors
Food additives and products
Cosmetics
Alcohol Accordingly, from the above list it can be seen that an industrial process material may be a standardised and/or undifferentiated solid, liquid or gaseous medium having a low inherent visual identity. The industrial process material may also include a mixture of two or more industrial process materials.

Depending on when the luminescent marker is added during the manufacturing procedure, the luminescent marker may be incorporated into the industrial process material or incorporated on the industrial process material. For example, where the industrial process material is produced as a solid the luminescent marker may be added and mixed with the industrial process material after its production. In this way the luminescent marker may coat the surface of the industrial process material (or a portion thereof) and therefore is incorporated "on" the industrial process material. An instance where the luminescent marker may be said to be incorporated "into" an industrial process material is where the luminescent marker is added during a process step and is located within the final material. A further example is where the luminescent marker is added after the production of an industrial process material in a manner in which it penetrates into the industrial process material.

Accordingly, the luminescent marker may be incorporated into and/or onto industrial process materials by physical incorporation and/or chemical incorporation. For example, physical incorporation may involve the physical trapping of luminescent dye molecules, particles, or aggregates, within the structure or structural make-up of a bulk material. Specific examples of physical incorporation include: the seeding of wet cement with microparticles of line phosphors prior to its casting; the driving of molecular luminescent dyes into the pore structure of timber under elevated pressure; and the suspension or dissolution of luminescent dyes in liquefied forms of commodity chemicals and preservatives.

Chemical incorporation may involve the creation of an attractive interaction between luminescent dye molecules, particles, or aggregates and the bulk material itself. Specific examples of chemical incorporation include: the adsorptive binding of molecular dyes to threads and yarns; the ion-paring of cationic luminescent dyes to negatively charged silica particles within the sand fillers used in cement; and the formation of attractive π-π interactions between aromatic dyes and bulk materials containing aromatic chemical groups.

In order for the luminescent marker to act as an effective marker for the methods of the present invention it must be present in detectable amounts. As used herein the term "trace amount" refers to an amount of luminescent marker which is present or required only in a minute amount so as not to be optically detectable in the presence of ambient light. Preferably, the amount is between 1 part per billion and less than 1% by mass of the industrial process material. It will be appreciated that the trace amount of the luminescent marker will exhibit fluorescence or phosphorescence but is not present in amounts which will cause the industrial process material to visibly fluoresce or phosphoresce under ambient light. Accordingly, the incorporation of the luminescent marker on or into the industrial process material according to the methods of the present invention does not provide the industrial process material with any visual identity when observed by the naked eye. As such, the presence of the luminescent marker does not affect the normal physical appearance of the industrial process material.

The methods of the present invention include the addition of luminescent markers which may be composed of a multitude of luminescent materials. Preferably when multiple luminescent materials form the luminescent marker the luminescent materials are selected such that these produce discrete electronic transitions (emission spectrum) and/or display varying intensity at these transitions. The use of such multiple luminescent materials enables the development of a versatile and dense encoding scheme whereby the characteristic emissions produced by the multiple luminescent materials incorporated on or into an industrial process material enables the identification of the material.

For example, one encoding scheme involves the addition or incorporation within the industrial process material of a luminescent marker comprising one or more luminescent materials in a variety of quantities to thereby impart the industrial process material with a unique luminescence spectrum. This spectral fingerprint may be exceedingly complex and detailed. As such, this unique spectrum may serve as a "fingerprint" that identifies the industrial process material. Such a spectrum may be stored in a digital form within a database library of such spectra and subsequently recognised from amongst this library by a suitable matching algorithm. Since the constituents and relative quantities of the luminescent materials in luminescent markers in such a spectral fingerprint can be varied in an almost unlimited number of ways, it follows that an extremely large number of codes can be devised to mark industrial process materials using this technique.

Another exemplar encoding scheme provides N number of luminescent materials as a luminescent marker (each having a discrete electronic transition), each having M distinguishable states, such that $M^n$ different states can be uniquely defined. In the case of M=2 where the two states could be the presence or absence of the luminescent material, the encoding scheme would thus be defined by a base 2 or binary code. In the case of M=3 where the three states could be the presence of a luminescent material at two distinguishable intensities or its absence, the encoding scheme would be defined by a base 3 code or tertiary code. Accordingly, higher codes can be formed which have the advantage over a binary order code in that fewer luminescent materials would be required to encode the same quantity of information.

A further exemplar method for coding involves using luminescent markers which impart the industrial process material with one or more unique qualities that are observable only under very specific conditions of measurement or detection. For example, luminescent markers may be used which emit highly distinctive spectra only under very particular conditions of temperature, pressure, concentration, salvation, vapour, magnetisation, or similar external physical condition. Under such a condition of observation, a distinctive spectrum is observed, or combined spectra are observed, and used to encode an industrial process material with a unique identity. Other examples in this respect include, but are not limited to the use of luminescent markers that: (i) emit light of particular polarisation or of particular anisotropy when irradiated with light having a particular polarisation or anisotropy (including light of no discernible polarisation or anisotropy), and (ii) glow with a particular spectrum or intensity profile when irradiated with light of one or more particular frequency and intensity profiles that are subjected to a particular, carefully controlled pulsing sequence.

A wide range of other encoding techniques may be used to impart industrial process materials with unique identities by the incorporation onto or into them of luminescent markers each of which can selectively comprise one or more luminescent materials.

The use of such codes in the methodology of the present invention provides identity to industrial process materials which ordinarily lack identity. This enables life-cycle tracking of the industrial process material which is especially important in monitoring the presence of those industrial process materials which are prone to being disposed of improperly or illegally at the end of its useful lifetime and may cause environment pollution. Tracking in this way also enables manufactures, consumers and law enforcement agencies to monitor any illicit trade in an industrial process material or illegal substitution for inferior materials which may affect manufacturers warranties and may also provide useful information when building a case to prosecute offenders.

It will be appreciated that the life-cycle tracking method will involve a step of identifying the industrial process material during a plurality of life-cycle stages, for example, at the point of manufacture to confer identity to the material, and after delivery to confirm that the material has not been substituted in transit. Also, the industrial process material may undergo processing to produce a product. The product can be a commodity product which, like the industrial process material, is standardised undifferentiated, substitutable, interchangeable, batch-processed in essentially identical form and available in bulk, or the product may be a high-value article. Accordingly, the life-cycle tracking method may involve an identifying step which involves detecting the luminescent marker in a commodity product or high-value product. Preferably, the method is used to track the industrial process material or the industrial process material and commodity products derived therefrom. Also it will be appreciated that once the industrial process material is transformed into a product, the detection of the luminescent marker will need to be performed on that product, if required.

This is generally conducted by removing samples of the product for analysis in a laboratory setting. The advantage of using embodiments of the portable reader system of the present invention however means that the luminescent marker can be detected in situ in the field, non-invasively, that is, without damaging the product.

Luminescent materials have previously been proposed for use in testing of biological materials. The methods of the present invention do not use the luminescent marker to biologically test the industrial process material.

A further advantage of embodiments of the methods of the present invention resides in stock control where large volumes of industrial process materials are produced on a daily basis. Again, because industrial process materials are inherently difficult to differentiate from one batch to the next, it is also difficult to conduct stocktakes and thus account for all the material produced. By adding unique luminescent codes to different batches of an industrial process material the whole stock control process may be modularised. This would be particularly important for the production of dangerous chemicals where it is a legislative requirement to account for all material produced and to provide information to the relevant authorities as to the whereabouts of the material at any given time.

A further related advantage of embodiments of the present invention resides in process control. For instance, in modularising the stock control process, as discussed above, it is easier to locate batches of a particular industrial process material which may be defective due to a processing error. Where procedures for preparing a particular industrial process material involve multiple process stages, process monitoring at each stage can be accomplished by adding a distinct luminescent marker during a particular process stage. In this way the quality of the final material can be accessed on a stage by stage basis whereby the efficiency of each stage can be monitored and process parameters varied if required.

Other more specific applications of the methods of the present invention are as follows:

a) For Concrete

To aid unambiguous batch and producer assignment in large concrete structures containing multiple batches, possibly from different manufacturers, a multiplicity of different luminescent materials in different quantities to form the luminescent marker may be employed to generate diverse and complex codes of the types described above in order to distinguish the different batches of concrete. As the strength of poured concrete can only be determined after an extended time of drying (typically 3 months), concrete batches that do not come up to specification can be accurately found, delimited, and replaced if required.

b) For Timber

A piece of timber can be treated such that a luminescent marker consisting of one or more luminescent materials is incorporated into the timber during preservation treatment. Thus, a piece of wood present in the frame of, say, a house can at any time be examined to assess the type of treatment used, and the success of the treatment both externally and internally. Moreover, the luminescent marker may be used to provide an indication of the treating company or of the plantation from which the timber originated, or of any other desirable variable.

More detailed information about the timber, its treatment, its origin, and its handling may be embedded through the use of coded combinations of a multiplicity of different luminescent materials. For example, to aid unambiguous batch, producer, or plantation assignment, diverse and complex combinations of multiple different luminescent dyes, as discussed above, may be added to preservatives and treated timber.

c) For Mineral Processing

A freshly extracted mineral ore, for example iron ore, may be marked by spraying with a suitable solution of a luminescent marker. Trace amounts of the luminescent marker may permeate and/or stick to the ore marking it unambiguously. The ore may subsequently be loaded, piecemeal, onto railway cars for transportation to an ore processing centre. The processing centre may be used by other mines. After the railway journey, the ore may be deposited in an ore field containing ores of all of the other mines. As the ore from separate mines may be required to be processed under slightly different conditions, it may be important to keep track of the origin of each ore batch. Immediately prior to processing, the ore can be therefore tested to confirm the presence of the luminescent marker, thereby identifying its origin and its optimum processing conditions. The processing technique is subsequently optimised for efficiency when treating the marked ore.

This process may be adapted to provide more detailed information regarding the particular batch of ore, such as the date, time, and the precise location (ore body) within the mine from which the ore was obtained. This may be achieved by spraying the ore with a solution of a luminescent marker incorporating various coded combinations of a multiplicity of luminescent materials as described above, and assigning each batch a unique identifying address.

d) For Fibres

A luminescent marker consisting of one or more luminescent materials may be selected which binds strongly to natural or synthetic fibres, threads, yarns, and the like. Within a particular dyeing plant, the luminescent marker may be incorporated at low levels within the dyes used to colour yarns, threads, and the like. It is preferred that when treated with these dyes, the yarns and threads bind the luminescent marker strongly. Using the portable reader of the present invention, the presence of the luminescent marker upon the fibres, yarns, or threads, may be unequivocally and unambiguously determined.

Alternatively, synthetic fibres may be produced under conditions in which a particular luminescent code or codes are incorporated as an integral part within the fibre. For example, synthetic fibres may be extruded or drawn such that they contain within them a mixture of one or more luminescent materials which provide a luminescent code or codes to identify them. Such fibres may subsequently be spun into yarns or threads and the like. Such yarns or threads may be incorporated at various levels and in various ways within fabrics or materials, where they may act as "marker fibres"; that is, where they act to provide the overall fabric or garment with an identity, a batch number, or similar property.

The above processes may be adapted to provide rudimentary or detailed information as required, including information regarding the origin and handling of the particular batch of fibres, yarns, threads, or information regarding the dye used, such as the date and time of dying, the dye manufacturer, and the dye batch number. This may be achieved by incorporating a luminescent marker consisting of a multiplicity of luminescent materials, as described above, within the dyes or within the fibres employed and assigning each combination of luminescent materials with a unique identifying address. In this way detailed information regarding, for example, the processing conditions, the dyes used, the dyeing plant employed, the fibre manufacturing technique, the fibre manufacturer, the fibre handling procedure, and the owner, manufacturer, or brand holder of the fibres, yarns, or threads, may be encoded into the materials.

e) For Foods

Luminescent markers respectively consisting of one or more luminescent materials approved for use as food additives may be incorporated within or upon foods or food products, or within or upon mass-produced medicines or pharmaceuticals. The trace incorporation of the luminescent marker may be used to provide rudimentary or detailed information, as required, regarding these industrial process materials, including information about the material, for example, the date and time of manufacture, the batch number, the method of manufacture, the method of packaging, and the identity of the manufacturer. This may be achieved by assigning each combination of the luminescent materials comprising the luminescent marker with a unique identifying address. This address may be connected to the above details in a database. Subsequent health and safety issues relating to a particular food, medicine or pharmaceuticals containing the luminescent materials may be investigated using information unambiguously embedded within the material.

f) For Explosives and Precursors Thereof.

Because of the risk of diversion for nefarious end, materials capable of being used in bomb-making must be closely monitored at all stages of their production, distribution, warehousing, and up to and including the point of their physical use and conversion into a form suitable for bomb-making. Such supplies, include a wide diversity of potentially explosive materials, ranging from military explosives, such as plastic explosives, through to fertilisers, such as ammonium nitrate. A key problem in this respect is distinguishing one sample of an explosive or potentially explosive material from another, identical sample. Thus, the physical production of an explosive (or potentially-explosive) material entails producing multiple, identical samples, which are collectively stored, counted, and distributed. Because each sample is identical to the next, a high possibility exists that it could be double-counted during stock-taking, or that it is not counted at all, thereby readily allowing for its unauthorised diversion to be undetected. Alternatively, it could be diverted for nefarious ends immediately after manufacture and prior to the first stocktaking, thereby resulting in its presence or absence not being recognised. In such cases, the diverted sample of the explosive material may be regarded or treated as though it was never produced. Another possibility is that a sample of the explosive material which has been diverted for nefarious purposes, may be replaced with an identical looking dummy material, whose non-explosive properties are not detected until very much later, by which time it is impossible to determine where in the manufacturing and distribution chain it was diverted. All of these possibilities arise because any one sample of the explosive material is indistinguishable from the next.

A solution to this difficulty is to provide each sample of the explosive or pre-explosive material with a unique identity, incontrovertibly embedded within all portions of the sample at the point of manufacture. This may be achieved by incorporating within the explosive material a luminescent marker which consists of a multiplicity of luminescent materials as described above, and assigning each combination of luminescent materials with a unique identifying address. In this way, each individual sample is infused, in a non-reversible way, with an address that distinguishes it from the next. During the production of the explosive or potentially explosive material, each subsequent sample may be provided with a new address in accordance with a pre-determined sequence of addresses. Where applicable, the addresses may be generated within the sample using an automated process in which trace amounts of luminescent markers, each comprising one or more pre-selected luminescent materials, are automatically added, according to a predetermined sequence, to the samples during manufacture. In this way, the sequence of addresses is therefore immune from human tampering.

Stocktaking may be undertaken at any stage in the manufacturing, warehousing, distribution, or subsequent logistical procedure, up the point of usage or of conversion to a form that is not suitable for bomb-making. Stocktaking may be modularised in that it involves checking whether all of the expected addresses are present. The absence of any one address immediately and unambiguously indicates an error whose origin can be directly and unequivocally pinpointed and investigated. Thus, double-counting or under-counting during stocktaking can be avoided or minimised. Moreover, diversion immediately after manufacture and prior to the first stocktaking is also prevented, as is substitution with a dummy material. By storing and monitoring the movement of each address, it is possible to monitor the distribution chain of each sample and determine whether it is ever diverted and, if so, to where it is diverted. In this way, weak links in the distribution chain can be readily identified and eliminated, thereby ensuring integrity in the distribution chain.

The application of the above process would be optimally achieved using a luminescent marker including one or more luminescent materials that are highly compatible with explosive materials in that they do not change the key physical properties of the explosive materials or react with these materials. Vacuum stability and friction sensitivity tests may be employed to assess the suitability of luminescent markers respectively comprising one or more luminescent materials for tracking explosive materials.

g) For Spray-Painting

Aerosol-type spray paints are widely used in the illegal creation of graffiti, a form of vandalism in which paint is applied to an object owned by another. In order to hinder graffiti and identify the perpetrators of such vandalism, individual cans of spray paints may be made to incorporate a luminescent marker consisting of one or more different luminescent materials in forensic quantities, so as to provide each individual can with a unique identifying address of the type described above. By maintaining a register of the purchasers of individual aerosol spray-paint cans, and by determining the address of the paint employed in the creation of graffiti (using the reader described above), it becomes possible to identify the individual can of spray paint used and also the individual who purchased it. In this way, it becomes possible to monitor the distribution chain of each individual can of spray paint to monitor, detect and prevent its illegal usage.

Furthermore, aerosol-type spray paints and lacquers may be used as a means of identifying the owner of fixed assets, such as scaffolding, tables and chairs, computers, and office furniture in general. At any stage in the future, the origin and owner of the asset can be determined by simply detecting the presence of the luminescent marker.

h) For Metal Parts

Industrial metals present special problems when it comes to marking due to the fact that their properties often depend on the presence of exceedingly small amounts of trace materials present in the alloy matrix. Incorporating even forensic or trace amounts of luminescent markers each including one or more luminescent materials, into a metal alloy may interfere with the desired properties of the metal. Furthermore, the bulk properties of metals are also greatly influenced by their crystal structure and crystal orientations. Once again, incorporating even forensic or trace amounts of a luminescent marker comprising one or more luminescent materials or other particles into the alloy matrix can interfere with the desired crystalline structure of the metal and influence the properties of the bulk metal in an undesirable way.

For these and other reasons, it has, until now, generally not been possible or cost-effective to readily incorporate luminescent materials into or onto metals because incorporating such materials throughout the metal matrix would have deleterious and unpredictable effects on the alloy matrix or on the crystalline properties of the metal or the metal alloy. Additionally, the luminescent properties of most luminescent materials are themselves typically degraded when they are physically incorporated into molten metals during their forming process.

However, techniques are now commercially available by which particles may be embedded into or onto the surface of metals by imparting them and their carrier media with specific ranges and combinations of kinetic and thermal energies. Such ranges of combinations of kinetic and thermal energies are typically, but not necessarily exclusively, created in industrial thermal and cold spray type processes. In these techniques, particles are, effectively, accelerated to high velocity and are then made to collide with a metal or metal alloy surface. The process of the collision embeds, impregnates, welds or otherwise affixes or attaches the particles to or in the surface, or near the surface of the metal or metal alloy. Such spray processes currently exist in the commercial environment where they are typically used for spraying materials onto metals for coating purposes, to replace electrolysis or to create other coatings that protect against oxidation, corrosion and wear. For example, commercially available cold spray (or cold gas-dynamic) technology can produce coatings with a gas-jet temperature that is lower than thermal spray processes such as powder flame, wire arc, plasma arc and high-velocity oxygen fuel spraying.

Such metal coating technology can be used to embed luminescent markers each consisting of one or more luminescent materials into metals and onto their surfaces by imparting them and their carrier media with specific kinetic and thermal energies. Although many luminescent materials are friable, meaning that their properties are typically degraded by stresses, such as the sheer stresses that are created in collisions, it has been found that many luminescent materials can be impacted or coated onto a metal using cold spray technology in such a way that they retain their luminescent properties without significant degradation.

Cold spray technology is therefore an example of a suitable conventional metal coating technique that can be used for incorporating, integrating, impregnating, welding or otherwise affixing or attaching luminescent markers each comprising one or more luminescent materials to metals in a way that has no significant deleterious effects to the metal or metal alloy's crystalline structure, or to the metal or metal alloy's thermal history. The key required mechanical properties of the metal are therefore unaffected by the marking process.

Moreover, such kinetic and thermal attachment methods may, additionally, be applied after the metal has been manufactured in a particular industrial process. For example, marking of this type may be applied to metal aircraft parts after their manufacture. This allows parts to be marked individually, in batches, or in any other format that may be desired.

DETAILED DESCRIPTION OF THE DRAWINGS

Figure 1:
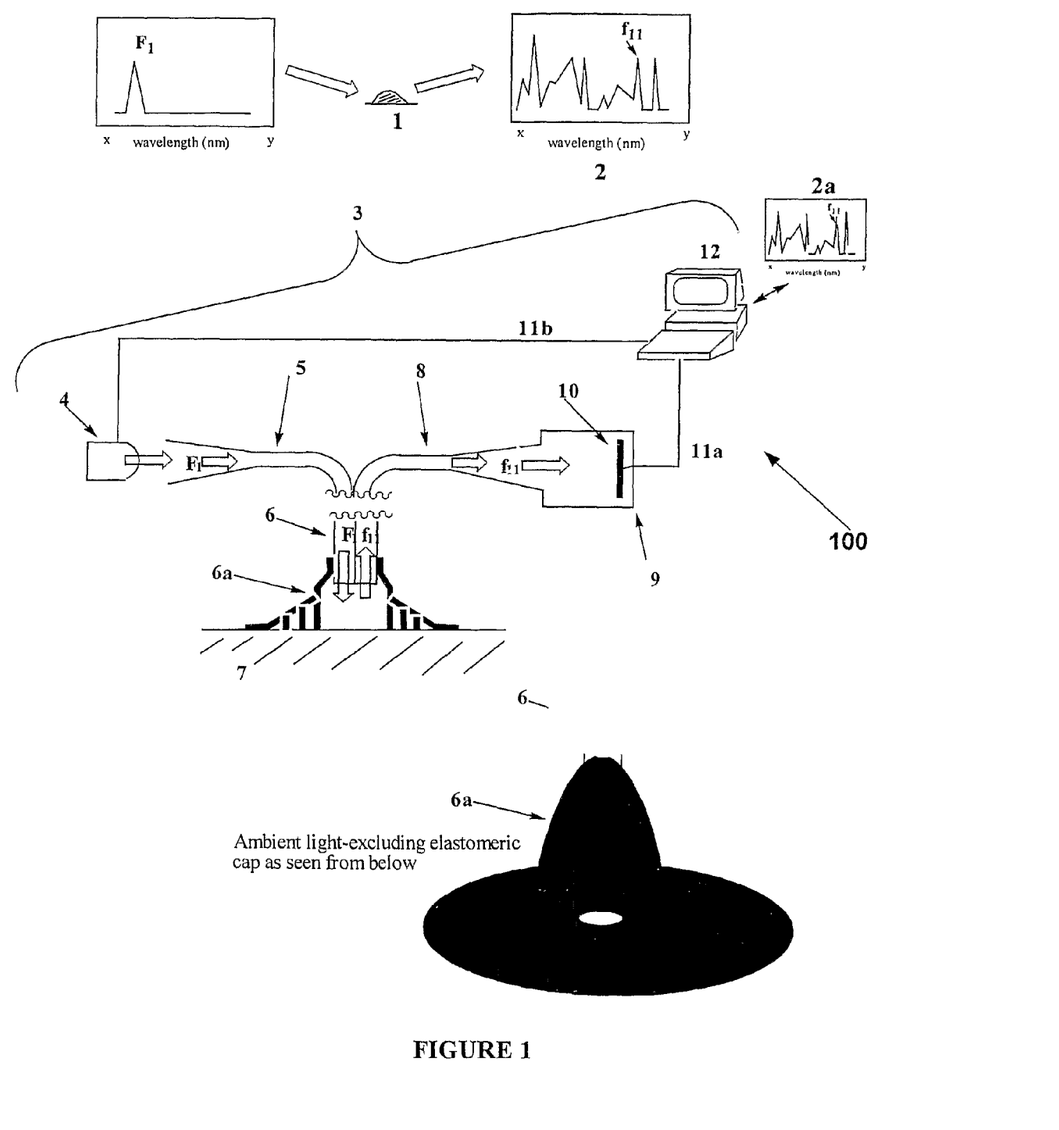
FIG. 1 is a schematic diagram of an embodiment of a system for field or on-site tracking, identification or authentication of an industrial process material.

FIG. 1 illustrates a system 100 for field or on-site tracking of a luminescent marker 1 incorporated in and/or on an industrial process material 7. When the luminescent marker 1 is irradiated with light of wavelength F1, it glows with the spectrum 2, containing the unique wavelength f11. In order to detect the presence of the luminescent marker 1 incorporated in or on an industrial process material 7, the material 7 is irradiated with F1 and any light emitted by the material 7 is collected and examined to see if it contains light of wavelength f11. To perform such an operation, a portable luminescence reader 3 can be used. In the reader 3, a light source 4 generates light of wavelength F1 when prompted by an attached computer 12. The computer 12 includes at least one processor (not shown) and processor instructions executable by the at least one processor. Optionally, the light source 4 may also generate light of other wavelengths F2, F3, F4 . . . Fm upon command by the computer 12. The light generated by the light source 4 is, optionally, collected and transported by a fibre optic or a bundle of fibre optic elements 5. Alternatively, the reader 3 may be so constructed that a fibre-optic collector 5 is replaced by a line-of-sight arrangement in which light is delivered directly to the material 7 by the light source 4.

At the head of the fibre optic or fibre optic bundle 6 (or at the reading aperture in the case where a line-of-sight arrangement is used), the light of wavelength F1 exits and falls upon the material 7 which contains trace amounts of the luminescent material 1. Because only trace (or forensic) amounts of the luminescent material 1 may be present in the material 7, it may glow only exceedingly weakly—far more weakly than even a small fraction of ambient light. Because ambient light may interfere with the detection process, it is excluded on each occasion that the reader 3 is used. This is achieved by fitting the head 6 (or the reading aperture) of the reader 3 with the elastomeric cap 6a (or shroud), which is so constructed that when the reader head is pressed up against any solid or particulate surface of the material 7, it moulds itself to the shape of the surface and substantially blocks all ambient light from entering the area immediately between the reader head 6 and the material 7. Any resulting glow emitted by the material 7 is collected by a second fibre optic or bundle of fibre optic elements 8 present in the head 6. These transport the collected light to a spectrometer 9, containing a suitable light-sensitive element 10 which is capable of detecting the presence of wavelength f11.

The spectrometer 9 can be any conventional instrument capable of detecting a particular frequency of light emitted by the material 7. Such an instrument can include, for example, at least the following elements: (a) a light-sensitive element 10 capable of electrically registering the presence of incident light; and (b) a frequency-controlling element capable of limiting, specifying, or controlling the frequency of the incident light. Examples of the light-sensitive element 10 include, for example: (a) a fluorescence spectrometer or similar device; (b) a suitable CCD chip or similar device; (c) a photodiode or similar device; (d) a photomultiplier tube or similar device, (e) a semiconductor or similar material capable of generating an electrical response when irradiated with light of selected frequency; and (f) a photoactive chemical capable of signalling the presence of light of a selected frequency in any way. Examples of the frequency-controlling element include, for example: (a) prisms and slits which disperse and separate the incident light into its constituent frequencies which can then each be measured separately; and (b) band-pass, cut-off, or other filters which selectively allow the passage of only certain frequencies of light, thereby allowing selective examination of these frequencies only.

The light-sensitive element 10 transmits measured data along cable 11a to an interfaced computer 12 which computes the spectrum or the detected frequency and determines whether the luminescent marker 1 is present based on the presence or absence of light having wavelength f11. The computer 12 may repeatedly switch on and switch off the light source 4 (using cable 11b) each time checking the presence or absence of a signal at the light-sensitive element 10 due to emission wavelength f11. The computer 12 may therefore mathematically verify the measured observation by repeating it or integrating the data. The computer 12 may also switch on and off the light source 4 at different times that it collects data from the light-sensitive element 10, thereby eliminating spurious or background data or generating a distinctive response or pattern of responses which is unique to the luminescent marker used.

As illustrated in FIG. 1 the reader 3 may be implemented using, for example: (i) a laptop computer or a personal digital assistant (PDA) 12 and appropriate wired or wireless connections 11; (ii) a USB2000 miniaturised spectrophotometer 9 supplied by Ocean Optics (Dunedin, Fla., USA) and (iii) a VSL-337 miniaturised ultra-violet laser 4 supplied by Laser Science Inc. and fitted with a fibre-optic connector 5.

Alternative light sources 4 can include, for example, one or more of the following: (i) light-emitting diodes (LEDs) operating at 250-365 nm, the latter being supplied by Nichia Corp., Japan, (ii) a PX2 pulsed Xenon light source supplied by Ocean Optics; and (iii) commercially available LEDs capable of generating a variety of visible and infra-red irradiation in the range 365-1100 nm. A variety of other solid state or incandescent light sources 4 may be employed. The light source may optionally be incorporated within the light-excluding elastomeric cap. A pulse generator, such as a Datapulse 100A supplied by Systron-Donner Corp., and a LED or other activating circuit may optionally be placed between the laptop computer 12 and the light source 4 in order to generate well-controlled light pulses.

Optical fibre cable 6 can be implemented, for example, as a QBIF400-UV-VIS, 400 micron thick bifurcated optical fibre cable supplied by Ocean Optics to carry exciting and emitted light. The fibre optic cable contains two layers of optic fibres: an inner bundle 5 around which is arranged an outer bundle 8. The terminus of the outer bundle is plugged into the fibre optic fitting on the laser. The terminus of the inner bundle 5 is plugged into the fibre optic fitting on the spectrophotometer 9. At the head of the fibre optic cable 6, the two fibre optic bundles are combined in a so-called "reflection probe". A reflection probe typically consists of a metal assembly which envelopes the two fibre optic bundles and provides a small lip beyond the end of the fibre optic. This lip can be angled (for example, at 30 degrees) when wanting to make measurements at these angles. In operation, reflection probes are held tight up against the sample to be analysed; the purpose of the lip is to eliminate as much of the external ambient light in the space between the fibre optic head 6 and the samples 7 as possible. Because the lips on reflection probes are metal, they can generally not provide a perfectly complementary fit with a sample surface. As such, they are unable to block out all of the ambient light present in the space between the reader head 6 and the sample 7. To combat this difficulty, manufacturers of such probes also supply large anodised aluminium blocks containing suitable receiving holes into which the reflection probes may snugly slide; these aluminium blocks are called "reflection probe holders". By virtue of their size (typically a 7 cm×4 cm footprint), these holders further block out the ambient light, but again not all of it.

To substantially eliminate the presence of ambient light and make possible the use of trace (or forensic) quantities of luminescent markers consisting of one or more luminescent materials, a light-excluding cap 6a made of a heavy rubber, is attached to the reader head 6 (or to the reader aperture in the case where a fibre-optic connector is not used). The cap 6a consists of a, black, conically-shaped rubber sleeve into which the reflection probe 6 (or the reader aperture) is pushed. The sleeve of the cap 6a fits the reflection probe 6 tightly. Near the bottom of the cone-like rubber sleeve of the cap 6a, a second, broader rubber cone is attached. This cone contains a series of concentric, circular rubber lips, each of which is capable of blocking out ambient light when the reader head is pressed against a sample surface. The rubber cap 6a eliminates ambient light during the measurement process.

The operation of the reader 3 may be controlled using OOIBase32™ or OOIChem Spectrometer operating software supplied by Ocean Optics. Alternatively, bespoke software may be used to control the operation of the reader 3. The software switches the laser 4 on and off, and collects and processes the data received from the spectrometer 9. The entire reader 3, including a controlling PDA computer and its battery, fits into a shoebox-sized volume making the reader 3 fully portable. The rubber cap 6a on the reader head 6 allows the reader to be routinely used in field operation, permitting reliable and ready, in-situ, determination of forensic quantities of luminescent materials present in industrial process materials. The rubber cap 6a facilitates such traceability. For example, the VSL laser 4 described above produces light of power approximately 10 microjoules per pulse. Using this light source 4 and the reader 3 and the rubber cap 6a, it is possible to detect, in routine field measurements, certain luminescence markers present in concentrations of 1-10 parts per million in commercially available concrete. This could not be achieved without substantially total exclusion of all ambient light.

The reader 3 may employ a detection algorithm (or protocol) to detect the presence of the luminescent marker in material 7. Numerous possible detection algorithms can be formulated. In one exemplar detection algorithm, the characteristic emission spectra of a plurality of luminescent markers 1 employed in the system 100 are stored in a database stored in the computer 12. By referring to the database, it is possible to identify the particular luminescent marker 1 present in an industrial process material 7. Thus, for example, when irradiated with light of frequency F1, luminescent marker 1 emits light having the spectrum shown in 2. This spectrum may be stored in a digital form in the computer 12 database as spectrum 2a. This database also contains the emission spectra of various other luminescent materials which comprise predetermined luminescent markers 7. When the industrial process material 7 is irradiated with light of frequency F1, it produces a spectrum. This spectrum is compared by the algorithm to each of the database spectra. If the observed spectrum fits 2a (within an expected variability range), the industrial process material 7 must clearly contain luminescent marker 1. By this means it becomes possible to detect the presence of a trace amount of a particular predetermined luminescent marker 1 within an industrial process material 7. This process may be repeated for various other combinations of luminescent markers 1 and industrial process materials 7.

Alternatively, the emission spectrum 2 may contain a distinctive and unique peak at frequency f1 which is not emitted by any of the other luminescent markers 1 in the system 100 upon illumination with light of frequency F1. The detection algorithm may operate by associating luminescent marker 1 with the presence of this peak in the emission spectrum resulting from irradiation with light of frequency F1. Thus, the detection algorithm may examine using conventional spectral matching techniques whether a peak of a particular intensity is observed at frequency f11 when the industrial process material 7 is illuminated with light of frequency F1. The presence of such a peak validates the presence of luminescent marker 1. The process may be repeated for other luminescent markers 1 comprising one or more luminescent materials having unique emission peaks.

The simultaneous presence in a luminescent marker 1 of a multiplicity of constituent luminescent materials 1,2,3,4, . . . n, each of which glows with a distinctly or mutually different emission wavelength, f11, f12, f13, f14, . . . f1$n$ when illuminated with light of wavelength F1, may be similarly determined. The reader 3 may be configured to carry out a routine in which the illuminating wavelength is sequentially changed to other wavelengths F2, F3, F4 . . . Fm, each of which cause one or more of a multiplicity of luminescent materials 1-$n$ to glow with distinctive wavelengths, fm1, fm2, fm3, fm4, . . . fmn. Each luminescent material 1-$n$ incorporated within the luminescent marker 1 of the industrial process material 7 in such a case may glow with at least one prominent and unique wavelength fmn when illuminated with light of a single wavelength Fm, but will not glow when irradiated with light of the other wavelengths Fm. Luminescent markers 1 comprising luminescent materials glowing with multiple wavelengths under multiple irradiation wavelengths can be used provided that their emissions are mutually non-interfering.

Figure 2:
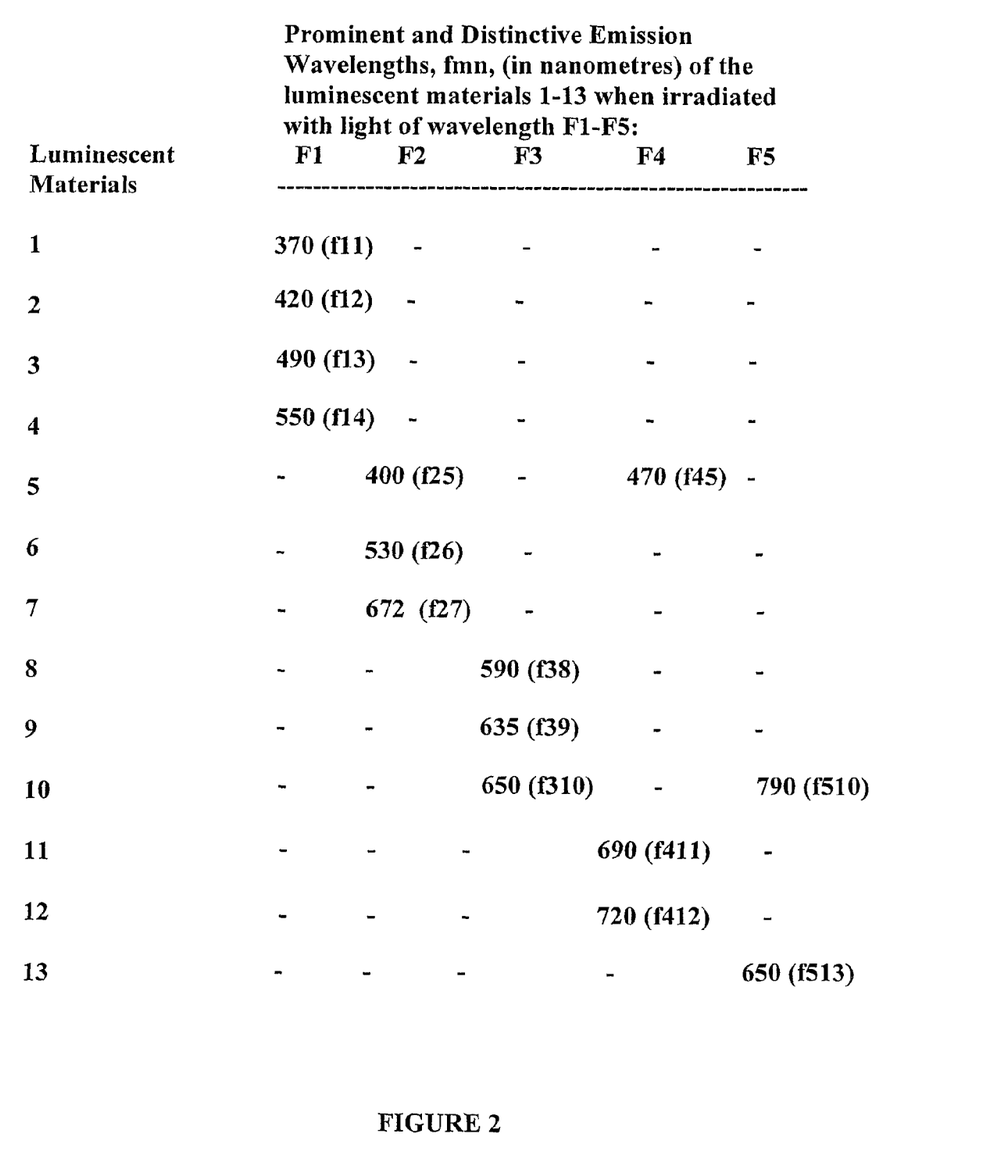
FIG. 2 is a table depicting mutually different emission wavelengths for 13 luminescent materials.

FIG. 2 depicts the emission properties of an example set of luminescent materials 1-13 which may be selectively used individually or in different combinations as a luminescent marker 1. Luminescent materials 1-4 glow strongly with distinctly different wavelengths when irradiated with F1, but do not noticeably glow when irradiated with F2-F5. Similarly, luminescent materials 6-7 glow distinctively when illuminated by F2, but not under any of the other irradiating wavelengths. Luminescent materials 8-9 glow effectively only when irradiated with F3 and their distinctive emission wavelengths are significantly different. Materials 11-12 emit, distinctively, only when irradiated with F4, while material 13 glows strongly only when irradiated with F5. Luminescent materials 5 and 10 glow strongly when irradiated with two different Fm wavelengths. However, their emission wavelengths are distinctive relative to those of other of the luminescent materials that glow when irradiated with these wavelengths. Their presence therefore does not introduce ambiguity when detecting different mixtures of materials 1-13.

By sequentially irradiating a sample of an industrial process material 7, which may contain a luminescent marker 1 consisting of a mixture of luminescent materials 1-13, with the wavelengths F1-F5 and determining the presence or absence of each of the expected wavelengths fmn, it is possible to determine which of the luminescent materials 1-13 are present. Since the presence or absence of each luminescent material provides a binary code (0=absent, 1=present), many combinations of these luminescent materials are possible. In this way, industrial process materials may be allocated a unique "address" (or code) which distinguishes them from all of the other possible addresses, thereby allowing differentiation of numerous, otherwise identical items marked with luminescent markers 1 comprising the luminescent materials 1-13.

Figure 3:
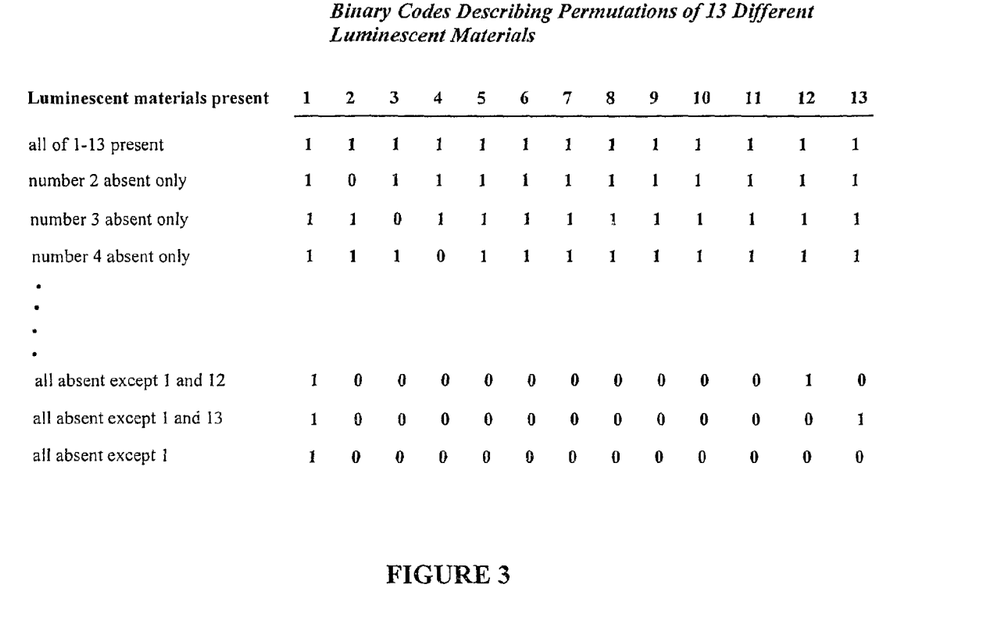
FIG. 3 is a table depicting binary code representations of the presence or absence of mutually different emission wavelengths for 13 luminescent materials.

FIG. 3 depicts a exemplar matrix of binary codes (or "addresses") deriving from the presence or absence of the above 13 different luminescent materials which make up the luminescent marker 1. Given that the absence of all of the luminescent materials does not provide unambiguous information, one of the luminescent materials must always be present; this material will ideally be a rare material, not freely available, and whose properties are not mimicked by any other luminescent material. In the example depicted in FIG. 3, constituent luminescent material 1 is chosen to be always present. As this material is not widely and generally available, it serves as a reference marker of the use of the technique. In the case of an industrial process material containing trace amounts of all 13 of the luminescent materials, the binary code 1111111111111 is generated, and this becomes the unique address for that industrial process material. If all but luminescent material 2 are present in another industrial process material, its address is 1011111111111. If all but luminescent material 3 are present in a further industrial process material, this provides it with the binary code address 1101111111111. This approach provides many different possible binary codes, thereby allowing differentiation of a large number of different industrial process materials, each marked with a luminescent marker 1 consisting of a different combination of the luminescent materials 1-13 and each having its own address.

The reader 3 as depicted in FIG. 1 may also be programmed to detect and compare the intensity of the emitted glow of one or more luminescent materials selectively comprised in the luminescent marker 1, according to an algorithm suitable to perform a particular process, quality, or logistic control task or tasks. Such an algorithm may involve measuring the digital amplitude of the signal received at a series of "expected" wavelengths in the ultra-violet, visible and infra-red regions when the light source is activated (or immediately thereafter, if it is pulsed). The "expected" wavelengths are those wavelengths at which any deliberately incorporated luminescent materials will glow strongly. For example, in the case of FIG. 2, the expected wavelengths are: f11, f12, f13, and f14 when illuminated with F1, f25, f26, and f27 when illuminated with F2, f8, f39, and f310 when illuminated with F3, f45, f411, and f412 when illuminated with F4, and f510 and f513 when illuminated with F5. For each illumination of the sample with light of wavelength Fm, the expected wavelengths are stored sequentially in a memory chip in the reader 3 along with their respective, measured, amplitude data. If the received amplitude for an expected wavelength crosses an empirically determined threshold level, a "1" is registered in the bin of the memory for that wavelength. If not, a "0" is registered. The resulting sequence of "1"'s and "0"'s is then compiled into a binary code of the type illustrated in FIG. 3. This process of compilation must take into account luminescent materials that glow at two or more different wavelengths fmn when illuminated at two or more different wavelengths Fm. For example, in FIG. 2, luminescent material 5 glows at wavelength f25 when illuminated with wavelength F2, and also glows at wavelength f45 when illuminated at wavelength F4. In order for a "1" to be registered overall for luminescent material 5, a "1" must be registered for each of: f25 when illuminated with F2 and f45 when illuminated with F4. In this way, a unique binary code of the type depicted in FIG. 3 is obtained.

If instead of comparing the simple presence or absence of luminescence materials ("0",s and "1",s), the relative intensities of their distinctive emission peaks are compared, then higher order coding is possible. For example, if the absence of a luminescent marker 1 is indicated by 0, the full presence (maximum intensity) of the marker by 2, and the presence at half-intensity by 1, then it is possible to make codes containing 0's, 1's and 2's (that is, a ternary code). Such codes contain more permutations and combinations then a binary code and are therefore correspondingly more complex.

In general, if, in a system containing q non-interfering luminescent markers, the maximum number of levels of intensity in each of the distinctive emission peaks that can be resolved is p, then a (p+1)-level code can be generated. Such a code will have $(p+1)^q$ possible permutations and combinations.

The detection algorithms and luminescent encoding techniques described above represent merely one method of creating luminescent codes with which to unambiguously identify industrial process materials 7 containing luminescent markers 1.

Figure 4:
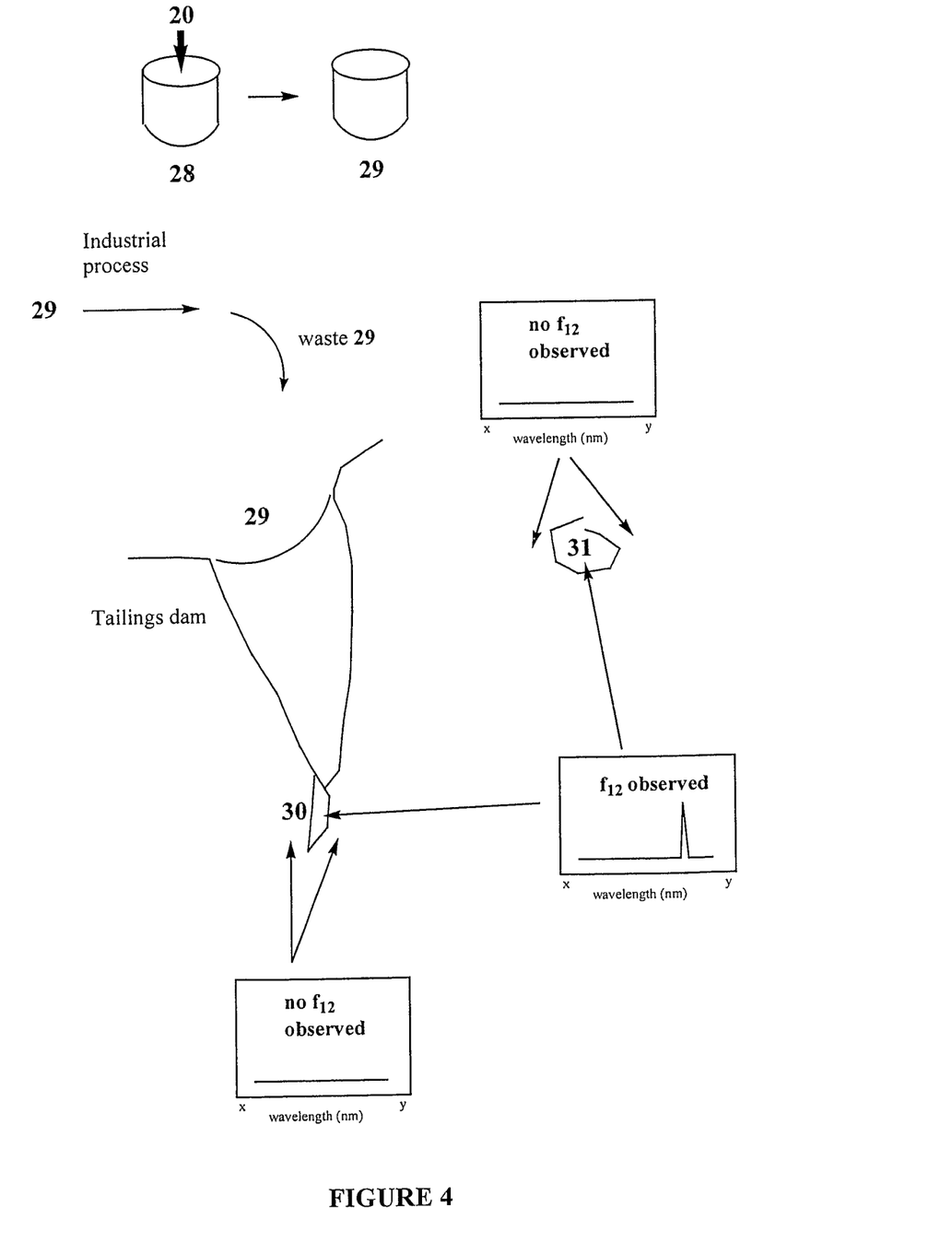
FIG. 4 is a schematic diagram depicting tracking of a commodity chemical using trace incorporation of luminescent markers.

Referring to FIG. 4, an industrial process material 28 includes, for example, a specialty or commodity chemical used in an industry such as the tanning of leather or the mining of a mineral comes in a water-based liquid form. A luminescent marker 20 comprising a water-soluble luminescent material is dissolved in chemical 28 in a trace amount. The resulting solution 29 is then used in the industrial process (for example, to treat and tan leather or to extract a mineral from an ore body), following which it is flushed into a waste dam 29 for treatment and destruction. The product of the industrial process (for example, the leather or the partially processed mineral) then contains a trace or small quantity of luminescent marker 20 and consequently glows with distinctive wavelength f12 when irradiated with light of wavelength F1. The intensity of this glow may provide information regarding the dosage of chemical 28 used and the uniformity of its use. Moreover, the movement and ultimate fate of the chemical 28 can be monitored by following the distribution of luminescent marker 20 to and about the waste dam 29. If the chemical 28 escapes from the waste dam 29, its leakage 30 into the environment may be traced and delimited by searching for luminescent marker 20 using the reader 3, tuned to be sensitive to the distinctive trace emissions of wavelength f12 under irradiation of wavelength F1.

For example, if chemical 28 enters the underground water table, its movement underground may be determined by looking for signs of luminescent marker 20 in a surface pool 31 at concentrations as low as 1 part per million. The originator and the cause of such a spill may thereby be readily detected and legal and environmental compliance measures taken. If the luminescent marker 20 is available only to the tannery or mine in question, the origin of the leather or partially processed mineral is, moreover, irretrievably marked upon the product. More detailed information may be embedded within the commodity or specialty chemical 28 by the use of luminescent markers 20 respectively consisting of coded combinations of a multiplicity of different luminescent materials as described above.

Figure 5A:
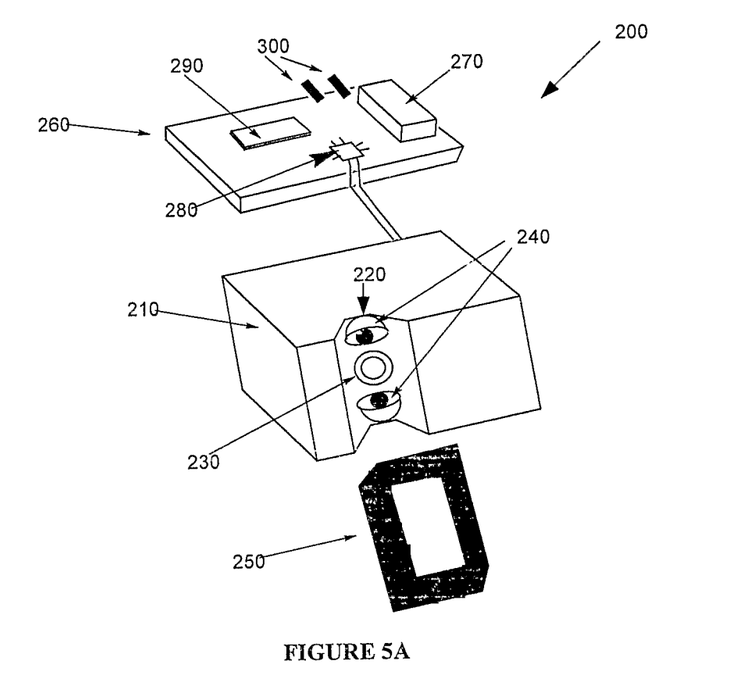
Figure 5B:
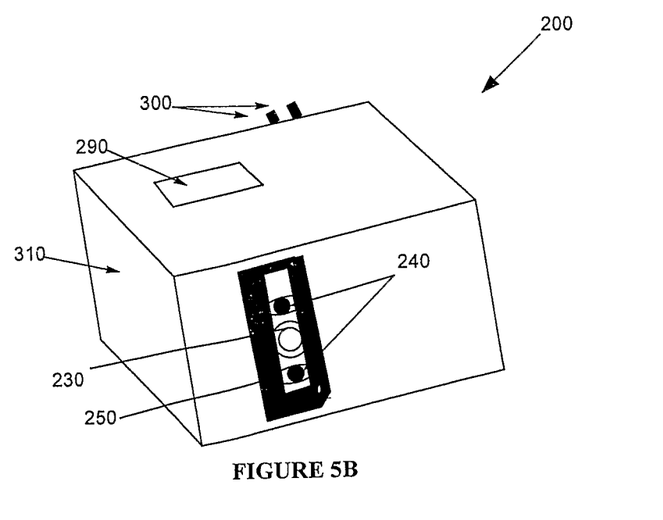
FIG. 5B is a perspective view of the reader of FIG. 5A in an assembled form.

FIGS. 5A and 5B illustrate an integrated portable luminescence reader 200 specially configured to non-destructively, optically detect trace amounts of luminescent markers in industrial process materials in situ in the field or on-site. The reader 200 includes a portable spectrometer 210, for example a portable Ocean Optics S1 spectrometer. The spectrometer 210 has a front recessed portion 220 in which an input optical port 230 is arranged. Two light-emitting diodes (LEDs) 240 are also arranged in the recessed portion 220 on opposite sides of the input optical port 230 of the spectrometer 210. One or both of the LEDs 240 can emit optical radiation having a wavelength range of about 250 nm to 365 nm. However, depending on a particular application, both of the LEDs 240 may emit optical radiation outside this wavelength range. Depending on the size and power of the LEDs and the applications involved, the reader 200 may include more than two LEDs 240.

The use of LEDs 240 tuned to emit optical radiation having a wavelength range of about 250 nm to 365 nm is advantageous because a substantial proportion of suitable luminescent markers absorb strongly within this wavelength range frequency range and consequently also emit as, or almost as intensely as they are capable of under these conditions. Thus, LEDs 240 operating in the wavelength range of about 250 nm to 365 nm can be used to excite a wide diversity of luminescent markers. Moreover, the use of such LEDs 240 makes it possible, in general, to use smaller amounts of luminescent markers than would be the case if LEDs 240 of other frequencies were used.

As illustrated in FIG. 5A, the LEDs 240 are arranged in the recessed portion 220 on either side of the input optical port 230 of the spectrometer 210 so as to illuminate an area directly adjacent and beyond the input optical port 230. When this area is illuminated, optical radiation emitted by any luminescent marker in this area will be partly directed toward and captured by the input optical port 230 of the spectrometer 210. Where necessary, a fibre optic "stub" or a small lens (not shown) may be fitted into the input optical port 230 to facilitate or enhance this light capture. The recessed portion of the housing 220 is surrounded by a flexible opaque shroud 250, for example a rubber shroud, that excludes ambient light from the input optical port 230 of the spectrometer 210 when the reader 200 is positioned on or adjacent to an industrial process material of interest. However in specific applications, other types of fittings that effectively exclude ambient light may be used. For example, a slot, fitted with a spring-loaded cover, that is custom-built to fit a material of interest may be used.

The spectrometer 210 and the LEDs 240 are operatively connected to and controlled by a custom-built circuit board 260 mounted on a surface of the spectrometer 210, along with a suitable small battery 270 which supplies power to the components of the reader 200. The circuit board 260 includes an LED driver circuit, which allows the LEDs 240 to be turned on and off by a microprocessor 280 included on the circuit board 260. The circuit board 260 also contains a display 290 and switches 300 to start/stop the reader 200 and perform other functions. The microprocessor 280 may be programmed with data, for example detection algorithms, via an attached data port. The detection algorithm employed by the reader 200 is downloaded onto the microprocessor 280 and then controls the actions of the reader 200 when activated. The reader 200 is enclosed in a custom-built housing 310 which comprises the outermost, visible body of the reader 200. This housing 310 surrounds the display 290, the rubber, light-excluding shroud 250, and the switches 300 in an aesthetically acceptable package. The reader 200, thus constructed, is small and fully portable, being about the size of a large pocket calculator. It is highly versatile, being able to apply a variety of operating actions and detection algorithms to detect a large diversity of luminescent markers. The reader 200 may be operatively connected to a wireless and/or wired network for wireless and/or wired data communications with remote computers, for example, a central server.

The invention will now be described in the following Examples. The Examples are not to be construed as limiting the invention in any way.

EXAMPLES

In examples 1-3 below, the luminescent marker 1 is pyrene, which absorbs light of wavelength 337 nm (F1 for the purposes of these examples), and glows with distinctive wavelength 367 nm (f11 for the purposes of these examples). Luminescent marker 2 is Ag-activated zinc sulfide, which absorbs light of wavelength 337 nm (F1), and distinctively emits light at 451 nm (f12 for the purposes of these examples). Luminescent marker 3 is Mn-activated magnesium fluorogeminate, which distinctively emits light at wavelength 658 nm (f13 for the purposes of these examples) when irradiated at 337 nm (F1 for the purposes of these examples). Luminescent marker 4 is anthracene, which absorbs light at 337 nm and distinctively emits at 425 nm (f14 for the purposes of these examples).

Example 1

Quality and Logistics Control of Concrete and Cement Products

Luminescent marker 1 (15 grams) is dissolved in a dichloromethane solution containing 1500 grams of the polymer, polymethylmethacrylate (PMMA). This solution is spray dried using a commercial spray-dryer, giving the luminescent marker 1 encapsulated with fine polymer beads containing in 1% wt/wt ratio. A trace amount of the luminescent marker 1 (1.5 grams within 150 grams of the PMMA polymer) is suspended in 2 litres of water and added to a single batch of concrete (7 cubic metres) within a mixer truck 13. The mixer is then run at maximum revolutions for 4 minutes, as is standard in the ready-mix concrete industry. The mixer is then set to slow revolutions and the truck proceeds to the pour site where the concrete batch is again mixed at maximum revolutions for 2 minutes. Following pouring and hardening, the precise location of the concrete batch and its boundaries within other poured batches of concrete may be determined by examining the surface of the concrete structure with a reader. The reader is as described in FIG. 1 and is tuned to produce F1 and detect f11. The reader consists of a laptop computer, a USB 2000 miniaturised spectrophotometer supplied by Ocean Optics and a VSL-377 miniaturised UV laser supplied by Laser Science Inc., fitted with a fibre optic connector, a Datapulse 100A pulse generator supplied by Systron-Donner Corp., optical fibre cable implemented as a QBIF400-UV-V15, 400 nm micron thick bifurcated optical fibre cable supplied by Ocean Optics (to carry light of excitation and emission. The fibre optic cable contains two layers of optic fibres, an inner bundle around which is arranged an outer bundle. The terminus of the outer bundle is plugged into the fibre optic fitting on the laser. The terminus of the inner bundle is plugged into the fibre optic fitting on the spectrophotometer. The probe head is fitted with a cap which consists of a cone-like rubber sleeve. Near the bottom of the cone-like rubber sleeve of the cap a second, broader rubber cone is attached. This cone contains a series of concentric, circular rubber lips, each of which is capable of blocking out ambient light when the reader head is pressed against a sample surface. The operation of the reader is controlled using OOIBase37™ operating software supplied by Ocean Optics. Detection is accomplished by sliding the head of the reader over the surface of the concrete, The presence of f11 in the emission spectrum of the concrete upon irradiation with F1 indicates the physical location of the batch. Other batches that do not contain the luminescent material 1 produce no clear signal f11 when irradiated with F1.

Unencapsulated luminescent materials 2 and 3 can be used to similarly mark concrete, with detection of f12 and f13 respectively, upon irradiation with F1.

Example 2

Process, Quality and Logistics Control of Timber and Timber Products

The timber product is to be marked with luminescent marker 4. Luminescent marker 4, is dissolved in a 0.003% wt/wt ratio in a commercial wood preservative solution consisting of white spirits and a powerful, soluble pesticide. The resulting mixture contains the preservative and trace amounts of luminescent marker 4.

A high-pressure cylinder for treating timber with preservative is charged with a timber piece (1 m×7 cm×7 cm). The cylinder is a non-commercial pilot plant used for testing purposes only. The cylinder is sealed and placed under a partial vacuum (85 KPa) for 15 minutes. The cylinder is then backfilled with the wood preservative solution containing the luminescent marker through an inlet valve. The preservative penetrates the timber carrying the luminescent marker with it. A positive pressure (700 KPa) is subsequently applied to the cylinder for 5 minutes to drive as much of the preservative solution as possible into the timber. Following release of this pressure, the cylinder is unsealed and the timber is removed.

Inspection of the surface of the timber using the reader, as described in Example 1, indicates that it glows uniformly with the wavelength f14 when illuminated with light of wavelength F1. Thus, the outer portions of the timber are evenly treated with the preservative solution. When the timber piece is sawn into the two pieces, inspection of a freshly cut face with the reader reveals that the inner surfaces also glow with wavelength f14 when illuminated with light of wavelength F1. Thus, this analysis reveals that, both the outer and inner portions of the timber were evenly marked with luminescent marker 4.

Example 3

Spray-Paints for Asset Management

An aerosol is charged with a propellant, a clear, air-drying lacquer or enamel, and luminescent markers 1 or 4, in 0.5% by weight (that is, 0.5 g per 100 grams of contents). The machine used to package the aerosol is the proprietary Color Pak 300 g aerosol paint filling system, which consists of a pneumatically operated aerosol filling machine, together with the proprietary prepacked mixture of solvents and propellants. The assets are sprayed with the aerosol and the lacquer/paint is allowed to dry. The identification of the wavelengths f11 and f14 are detected by playing the reader (which emits wavelength F1, as described in Example 1) over the surface of the assets.

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method of marking bulk, undifferentiated industrial process material, the method including encoding the industrial process material with a luminescent marker in a trace amount sufficient to be non-destructively optically detectable in and/or on the industrial process material in situ in the field or on-site, wherein the trace amount of the luminescent marker is used to track, identify or authenticate the industrial process material for at least two of material control, inventory control, stock control, process control, logistics control, quality control and pollution control, wherein the luminescent marker includes a multiplicity of constituent luminescent materials, the constituent luminescent materials being inorganic phosphorescent phosphors, and wherein each luminescent material of the constituent luminescent materials has a phosphorescence emission spectrum including one or more distinct peaks that are unique to that luminescent material, such that emissions from respective luminescent materials are mutually non-interfering when subjected to pulses of light in a predetermined pulsing sequence and detectable through gating that involves detection at exactly one time value.

2. A method according to claim 1, wherein the industrial process material is at least one of cement, concrete, timber, mineral ore, plastic, fiber, food, paint, metal, explosive-precursor material and explosive material.

3. A method according to claim 1, wherein the luminescent marker is optically detected in situ in the field or on-site with a portable or fixed luminescence reader.

4. A method according to claim 1, wherein the emissions are a unique luminescent response that represents a unique code corresponding to the industrial process material.

5. A method according to claim 4, wherein the unique code is further represented by one or more predetermined luminescence detection parameters and/or a luminescence detection algorithm.

6. A method according to claim 4, wherein the unique code is further represented by the relative presence and/or absence of a plurality of luminescent emission and/or excitation profiles respectively associated with a corresponding plurality of luminescent materials that comprise the luminescent marker.

7. A method according to claim 1, wherein information relating to the industrial process material and its conferred unique luminescent response are associatively stored in a database.

8. A method according to claim 1, wherein the trace amount of the luminescent marker is further usable to track the industrial process material through a plurality of life-cycle stages, including at least two of raw material acquisition, processing, manufacturing, formulation, transportation, distribution, use, reuse, maintenance, recycling, disposal and waste management.

9. A method according to claim 1, further including tracking a product, part or structure formed from the industrial process material without damaging the product, part or structure.

10. A method according to claim 1, wherein the industrial process material is acquired or processed in a plurality of batches and a unique luminescent response is conferred on individual batches of the industrial process material to enable inventory control or stock control thereof.

11. A method according to claim 1, wherein the industrial process material has low inherent visual identity.

12. A method according to claim 11, wherein the industrial process material is selected from the group consisting of a material used for construction, a material used for structural and non-structural applications in transportation vehicles, a material used for industrial manufacturing of goods, components, clothing, and chattels, a material used in the industrial manufacturing of computers and information technology-based items, a material used for large-scale industrial packaging of goods, components and chattels, a material used in primary and energy industries, and a material used in miscellaneous industrial manufacturing.

13. A method according to claim 1, wherein the luminescent marker is optically detectable using optical radiation having a wavelength range of about 250 nm to about 365 nm.

* * * * *